(12) United States Patent
Chen et al.

(10) Patent No.: US 8,709,465 B2
(45) Date of Patent: Apr. 29, 2014

(54) DIAZENIUMDIOLATED PHOSPHORYLCHOLINE POLYMERS FOR NITRIC OXIDE RELEASE

(75) Inventors: Mingfei Chen, Santa Rosa, CA (US);
David Shumaker, Santa Rosa, CA (US);
Peiwen Cheng, Santa Rosa, CA (US);
Kishore Udipi, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 939 days.

(21) Appl. No.: 12/422,425

(22) Filed: Apr. 13, 2009

(65) Prior Publication Data

US 2010/0262238 A1    Oct. 14, 2010

(51) Int. Cl.
  *A61F 2/02* (2006.01)
  *A61F 2/04* (2013.01)
  *A61K 31/436* (2006.01)
  *C08F 130/02* (2006.01)

(52) U.S. Cl.
  USPC ............. 424/423; 623/11.11; 525/326.6

(58) Field of Classification Search
  None
  See application file for complete search history.

(56) References Cited

U.S. PATENT DOCUMENTS

| | | |
|---|---|---|
| 4,954,526 A | 9/1990 | Keefer |
| 5,039,705 A | 8/1991 | Keefer et al. |
| 5,155,137 A | 10/1992 | Keefer et al. |
| 5,212,204 A | 5/1993 | Keefer et al. |
| 5,250,550 A | 10/1993 | Keefer et al. |
| 5,268,465 A | 12/1993 | Bredt et al. |
| 5,362,718 A | 11/1994 | Skotnicki et al. |
| 5,366,997 A | 11/1994 | Keefer et al. |
| 5,380,758 A | 1/1995 | Stamler et al. |
| 5,405,919 A | 4/1995 | Keefer et al. |
| 5,428,070 A | 6/1995 | Cooke et al. |
| 5,468,630 A | 11/1995 | Billiar et al. |
| 5,525,357 A | 6/1996 | Keefer et al. |
| 5,574,068 A | 11/1996 | Stamler et al. |
| 5,583,101 A | 12/1996 | Stamler et al. |
| 5,650,447 A | 7/1997 | Keefer et al. |
| 5,658,565 A | 8/1997 | Billiar et al. |
| 5,665,077 A | 9/1997 | Rosen et al. |
| 5,718,892 A | 2/1998 | Keefer et al. |
| 5,891,459 A | 4/1999 | Cooke et al. |
| 5,900,246 A | 5/1999 | Lambert |
| 5,945,452 A | 8/1999 | Cooke et al. |
| 6,015,815 A | 1/2000 | Mollison |
| 6,110,453 A | 8/2000 | Keefer et al. |
| 6,153,588 A | 11/2000 | Chrzan et al. |
| 6,290,981 B1 | 9/2001 | Keefer et al. |
| 6,329,386 B1 | 12/2001 | Mollison |
| 6,403,759 B2 | 6/2002 | Stamler et al. |
| 6,610,660 B1 | 8/2003 | Saavedra et al. |
| 6,673,891 B2 | 1/2004 | Stamler et al. |
| 6,706,274 B2 | 3/2004 | Herrmann et al. |
| 6,737,447 B1 | 5/2004 | Smith et al. |
| 6,759,430 B2 | 7/2004 | Anggard et al. |
| 6,841,166 B1 | 1/2005 | Zhang et al. |
| 6,875,840 B2 | 4/2005 | Stamler et al. |
| 6,911,478 B2 | 6/2005 | Hrabie et al. |
| 6,949,530 B2 | 9/2005 | Hrabie et al. |
| 6,951,902 B2 | 10/2005 | McDonald et al. |
| 7,070,798 B1 | 7/2006 | Michal et al. |
| 7,087,709 B2 | 8/2006 | Stamler et al. |
| 7,105,502 B2 | 9/2006 | Arnold et al. |
| 7,378,105 B2 | 5/2008 | Burke et al. |
| 2002/0094985 A1 | 7/2002 | Herrmann et al. |
| 2004/0037836 A1 | 2/2004 | Stamler et al. |
| 2004/0171589 A1 | 9/2004 | Herrmann et al. |
| 2004/0180131 A1 | 9/2004 | Cheng |
| 2005/0171596 A1 | 8/2005 | Furst et al. |
| 2005/0203069 A1 | 9/2005 | Arnold et al. |
| 2005/0265958 A1 | 12/2005 | West et al. |
| 2005/0281866 A1 | 12/2005 | Jarrett et al. |
| 2006/0008529 A1 | 1/2006 | Meyerhoff et al. |
| 2006/0099235 A1 | 5/2006 | Blakstvedt et al. |
| 2006/0121089 A1 | 6/2006 | Michal et al. |
| 2006/0195142 A1 | 8/2006 | Shalaby |
| 2006/0251824 A1 | 11/2006 | Boulais et al. |
| 2007/0014828 A1 | 1/2007 | Fitzhugh |
| 2007/0053952 A1 | 3/2007 | Chen et al. |
| 2007/0185561 A1 | 8/2007 | Schmitz et al. |
| 2007/0264225 A1 | 11/2007 | Cheng et al. |
| 2008/0220040 A1 | 9/2008 | Cheng et al. |
| 2008/0220048 A1 | 9/2008 | Chen et al. |
| 2008/0286332 A1* | 11/2008 | Pacetti .................. 424/424 |
| 2009/0028966 A1 | 1/2009 | Chen et al. |
| 2009/0222088 A1 | 9/2009 | Chen et al. |
| 2009/0232863 A1 | 9/2009 | Cheng et al. |
| 2009/0232868 A1 | 9/2009 | Chen et al. |

FOREIGN PATENT DOCUMENTS

| | | |
|---|---|---|
| EP | 0945148 | 9/1999 |
| EP | 0992252 | 4/2000 |
| EP | 1300424 | 4/2003 |
| EP | 1623728 | 2/2006 |

(Continued)

OTHER PUBLICATIONS

Frost, Biomaterials, 26, 2005.*
Mintz G et al: Intravascular Ultrasound in the Drug-Eluting Stent Era, Aug. 1, 2006, pp. 421-429, Journal of the American College of Cardiology, Elsevier New York, NY, US.
Malik N et al: "Phosphorylcholine-coated stents in porcine coronary arteries: in vivo assessment of biocompatibility," The Journal of Invasive Cardiology, vol. 13, No. 2 Mar. 2001, pp. 193-201.

(Continued)

*Primary Examiner* — Robert A Wax
*Assistant Examiner* — William Craigo

(57) ABSTRACT

The present disclosure in a broad aspect provides for diazeniumdiolated phosphorylcholine polymers and associated methods for achieving nitric oxide release. The present polymers have superior biocompatibility and are useful for coating or fabricating medical devices such as a vascular stent.

19 Claims, No Drawings

(56) References Cited

FOREIGN PATENT DOCUMENTS

| | | |
|---|---|---|
| WO | WO95/24908 | 9/1995 |
| WO | WO96/15797 | 5/1996 |
| WO | WO99/01427 | 1/1999 |
| WO | WO01/10344 | 2/2001 |
| WO | WO2005/039664 | 5/2005 |
| WO | WO2005/081752 | 9/2005 |
| WO | WO 2005/089855 | 9/2005 |
| WO | WO2006/037105 | 4/2006 |
| WO | WO 2007/024492 | 3/2007 |
| WO | WO2007/024501 | 3/2007 |
| WO | WO 2007/004935 | 4/2007 |
| WO | WO2007/053292 | 5/2007 |
| WO | WO2007/053578 | 5/2007 |
| WO | WO 2007053292 A2 * | 5/2007 |
| WO | WO 2008/112391 | 9/2008 |
| WO | WO 2009/014829 | 1/2009 |
| WO | WO 2009/117183 | 9/2009 |

OTHER PUBLICATIONS

Kuiper KKJ et al: Phosphorylocholine-coated metallic stents in rabbit iliac and porcine coronary arteries:, Scandinvavian Cardiovascular Journal, vol. 32, No. 5, 1998, pp. 261-268.

U.S. Appl. No. 12/340,089, filed Dec. 19, 2008.

Washington State Univ. Lecture, Chemistry 240, Summer 2001, http://chemistry2.csudh.edu/rpendarvis/aminrxn.html.

Reynolds et al., "Nitric Oxide Releasing Polyurethanes with Covalently Linked Diazeniumdiolated Secondary Amines" Biomacromolecules 2006, 7, 987-994.

Tashiro et al., "Removal of Methyl Orange by Systems of Insoluble Poly(Glycidyl Methacrylate)-G-Tetraethylene-Pentamine and—G-Polyethyleneimines", Research Institute for Polymers and Textiles, 205 (1993) 31-45.

Hrabie et al., "New Nitric Oxide-Releasing Zwitterions Derived from Polyamines" J. Org. Chem, 1993, 58, 1472-1476.

Drago et al., "The Reaction of Notrogen(II) Oxide with Diethylamine" Contribution from the W.A. Noyes Laboratory, University of Illinois, Jun. 24, 1959.

Parzuchowski et al., "Synthesis of Potentially More Blood Compatible Nitric Oxide Releasing Acrylic Copolymers" Polymer Preprints, 2001, 42(1), pp. 448-449.

Williams et al. "Nitric Oxide-Releasing Nonsteroidal Anti-Inflammatory Drugs (NSAIDs) Alter the Kinetics of Human Colon Cancer Cell Lines More effectively then Traditional NSAIDs: Implications for Colon Cancer Chemoprevention" Cancer Research, 61, 3285-3289, Apr. 15, 2001, pp. 3285-3289.

Frost et al. "Polymers Incorporating Nitric Oxide Releasing/Generating Substances for Improved Biocompatibility of Blood-Contacting Medical Devices" Biomaterials 26 (2005) 1685-1693.

Deng et al., "Polymerization of Lactides and Lactones 11. Ring-Opening Polymerization of x-Acetyl-y-Butyrolactone and Copolymerization with B-Butyrolactone" European Polymer Journal, 36 (2000) 2739-2741.

Lovric et al., "Scope and Limitations of Sodium and Potassium Trimethylsilanolate as Reagents fro Conversion of Esters to Carboxylic Acids" Croatica Chemica Acta, CCACAA 80 (1), 109-115 (2007).

Kireev et al., "Polymerization of Methyl Methacrylate and Vinyl Acetate Initiated by the Manganese Carbonyl-1,2-Epoxy-4,4,4-Trichlorobutance System" Polymer Science, Ser. B, 2006, vol. 48, Nos. 5-6, pp. 138-141.

Liu et al., "Diethylenetriamine-Grafted Poly(Glycidyl Methacrylate) Adsorbent for Effective Copper Ion Adsorption" Journal of Colloid and Interface Science 303 (2006) 99-108.

Oh et al., "Spontaneous Catalytic Generation of Nitric Oxide from S-Nitrosothiols at the Surface of Polymer Films Doped with Lipophilic Copper (II) Complex" J. Am. Chem. Soc. 125, pp. 9552-9553, 2003.

Abizaid, Alexandre MD "Novel Approaches to New DES Therapies: Where are we Going?" ACC 2007, New Orleans.

Pasterkamp et al., "Atherosclerotic Plaque Rupture: an Overview" J Clin Basic Cardiol, 2000; 3: pp. 81-96.

Wolfe et al., "Cyclic Hydroxamates, Especially Multiply Substituted [1,2] Oxazinan-3-Ones" Can. J. Chem. 81: 937-960 (2003).

* cited by examiner

DIAZENIUMDIOLATED PHOSPHORYLCHOLINE POLYMERS FOR NITRIC OXIDE RELEASE

FIELD OF THE INVENTION

The present disclosure generally related to biocompatible nitric oxide donating polymers having at least one diazeniumdiolated phosphorylcholine functional group useful for fabricating or coating medical devices.

BACKGROUND OF THE INVENTION

Nitric oxide (NO) is a simple diatomic molecule that plays a diverse and complex role in cellular physiology. Less than 25 years ago NO was primarily considered a smog component formed during the combustion of fossil fuels mixed with air. However, as a result of the pioneering work of Ferid Murad et al. it is now known that NO is a powerful signaling compound and cytotoxic/cytostatic agent found in nearly every tissue including endothelial cells, neural cells and macrophages. Mammalian cells synthesize NO using a two step enzymatic process that oxidizes L-arginine to N-ω-hydroxy-L-arginine, which is then converted into L-citrulline and an uncharged NO free radical. Three different nitric oxide synthase enzymes regulate NO production. Neuronal nitric oxide synthase (NOSI, or nNOS) is formed within neuronal tissue and plays an essential role in neurotransmission; endothelial nitric oxide synthase (NOS3 or eNOS), is secreted by endothelial cells and induces vasodilatation; inducible nitric oxide synthase (NOS2 or iNOS) is principally found in macrophages, hepatocytes and chondrocytes and is associated with immune cytotoxicity.

Neuronal NOS and eNOS are constitutive enzymes that regulate the rapid, short-term release of small amounts of NO. In these minute amounts NO activates guanylate cyclase which elevates cyclic guanosine monophosphate (cGMP) concentrations which in turn increase intracellular $Ca^{2+}$ levels. Increased intracellular $Ca^{2+}$ concentrations result in smooth muscle relaxation which accounts for NO's vasodilating effects. Inducible NOS is responsible for the sustained release of larger amounts of NO and is activated by extracellular factors including endotoxins and cytokines. These higher NO levels play a key role in cellular immunity.

Medical research is rapidly discovering therapeutic applications for NO including the fields of vascular surgery and interventional cardiology. Procedures used to clear blocked arteries such as percutaneous transluminal coronary angioplasty (PTCA) (also known as balloon angioplasty) and atherectomy and/or stent placement can result in vessel wall injury at the site of balloon expansion or stent deployment. In response to this injury a complex multi-factorial process known as restenosis can occur whereby the previously opened vessel lumen narrows and becomes re-occluded. Restenosis is initiated when thrombocytes (platelets) migrating to the injury site release mitogens into the injured endothelium. Thrombocytes begin to aggregate and adhere to the injury site initiating thrombogenesis, or clot formation. As a result, the previously opened lumen begins to narrow as thrombocytes and fibrin collect on the vessel wall. In a more frequently encountered mechanism of restenosis, the mitogens secreted by activated thrombocytes adhering to the vessel wall stimulate over-proliferation of vascular smooth muscle cells during the healing process, restricting or occluding the injured vessel lumen. The resulting neointimal hyperplasia is the major cause of a stent restenosis.

Recently, NO has been shown to significantly reduce thrombocyte aggregation and adhesion; this combined with NO's directly cytotoxic/cytostatic properties may significantly reduce vascular smooth muscle cell proliferation and help prevent restenosis. Thrombocyte aggregation occurs within minutes following the initial vascular insult and once the cascade of events leading to restenosis is initiated, irreparable damage can result. Moreover, the risk of thrombogenesis and restenosis persists until the endothelium lining the vessel lumen has been repaired. Therefore, it is essential that NO, or any anti-restenotic agent, reach the injury site immediately.

One approach for providing a therapeutic level of NO at an injury site is to increase systemic NO levels prophylactically. This can be accomplished by stimulating endogenous NO production or using exogenous NO sources. Methods to regulate endogenous NO release have primarily focused on activation of synthetic pathways using excess amounts of NO precursors like L-arginine, or increasing expression of nitric oxide synthase (NOS) using gene therapy. U.S. Pat. Nos. 5,945,452, 5,891,459 and 5,428,070 describe sustained NO elevation using orally administered L-arginine and/or L-lysine. However, these methods have not been proven effective in preventing restenosis. Regulating endogenously expressed NO using gene therapy techniques remains highly experimental and has not yet proven safe and effective. U.S. Pat. Nos. 5,268,465, 5,468,630 and 5,658,565, describe various gene therapy approaches.

Exogenous NO sources such as pure NO gas are highly toxic, short-lived and relatively insoluble in physiological fluids. Consequently, systemic exogenous NO delivery is generally accomplished using organic nitrate prodrugs such as nitroglycerin tablets, intravenous suspensions, sprays and transdermal patches. The human body rapidly converts nitroglycerin into NO; however, enzyme levels and co-factors required to activate the prodrug are rapidly depleted, resulting in drug tolerance. Moreover, systemic NO administration can have devastating side effects including hypotension and free radical cell damage. Therefore, using organic nitrate prodrugs to maintain systemic anti-restenotic therapeutic blood levels is not currently possible.

Therefore, considerable attention has been focused on localized, or site specific, NO delivery to ameliorate the disadvantages associated with systemic prophylaxis. Implantable medical devices and/or local gene therapy techniques including medical devices coated with NO-releasing compounds, or vectors that deliver NOS genes to target cells, have been evaluated. Like their systemic counterparts, gene therapy techniques for the localized NO delivery have not been proven safe and effective. There are still significant technical hurdles and safety concerns that must be overcome before site-specific NOS gene delivery will become a reality.

However, significant progress has been made in the field of localized exogenous NO application. To be effective at preventing restenosis an inhibitory therapeutic such as NO must be administered for a sustained period at therapeutic levels. Consequently, any NO-releasing medical device used to treat restenosis must be suitable for implantation. An ideal candidate device is the vascular stent. Therefore, a stent that safely provides therapeutically effective amounts of NO to a precise location would represent a significant advance in restenosis treatment and prevention.

Nitric oxide-releasing compounds suitable for in vivo applications have been developed by a number of investigators. As early as 1960 it was demonstrated that NO gas could be reacted with amines, for example, diethylamine, to form NO-releasing anions having the following general formula R—R'N—N(O)NO. Salts of these compounds could spontaneously decompose and release NO in solution.

Nitric oxide-releasing compounds with sufficient stability at body temperatures to be useful as therapeutics were ultimately developed by Keefer et al. as described in U.S. Pat. Nos. 4,954,526, 5,039,705, 5,155,137, 5,212,204, 5,250,550, 5,366,997, 5,405,919, 5,525,357 and 5,650,447 all of which are herein incorporated by reference.

The in vivo half-life of NO, however, is limited, causing difficulties in delivering NO to the intended area. Therefore NO-releasing compounds which can produce extended release of NO are needed. Several exemplary NO-releasing compounds have been developed for this purpose, including for example a NO donating aspirin derivative, amyl nitrite and isosorbide dinitrate. Additionally, biocompatible polymers having NO adducts (see, for example, U.S. Patent Publications 2006/0008529 and 2004/0037836) and which release NO in a controlled manner have been reported.

Secondary amines have the ability to bind two moles of NO and release them in an aqueous environment. The general structure of exemplary secondary amines capable of binding two NO molecules is depicted in Formula 1, referred to hereinafter a diazeniumdiolate, (wherein M is a counterion, and can be a metal, with the appropriate charge, or a proton and wherein $R^1$ and $R^2$ are generic notation for organic and inorganic chemical groups). Exposing secondary amines to basic conditions while incorporating NO gas under pressure leads to the formation of diazeniumdiolates.

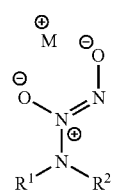

Formula 1

Polymers with diazeniumdiolate functional groups are capable of spontaneous release of nitric oxide under physiological conditions. Diazeniumdiolate is typically formed by a solution diazeniumdiolation process under strong basic conditions. Generally, the diazeniumdiolate polymers have poor solubility in organic solvent.

Biocompatibility of any medical device which is put inside a patient can present a problem. If the body rejects a medical device, such as a vascular stent, procedures performed to treat vascular diseases may be considered a failure. This is the case even if NO is released in suitable amounts and at proper locations by the medical device. Thus, there is an unmet need in the art to have materials which are NO releasing but also have superior biocompatibility.

SUMMARY OF THE INVENTION

The present disclosure addresses the long-felt need for materials which are biocompatible and release therapeutic nitric oxide (NO) from diazeniumdiolated functional groups. Phosphorylcholine (PC) is a cell membrane component. Polymers with PC functional groups have proved to be very biocompatible. Such materials have been used in medical devices such as drug eluting stents and contact lenses. The present disclosure generally relates to methods and related material resulting from the fact that PC can be diazeniumdiolated to release nitric oxide and after NO release, the diazeniumdiolate potentially can revert back to the PC functional group. Thus, even after NO release is completed, medical devices having the present polymers retain superior biocompatibility.

In one embodiment, the present disclosure relates to a nitric oxide donating polymer comprising a biocompatible polymer having at least one diazeniumdiolated phosphorylcholine functional group. In another embodiment, the biocompatible polymer having at least one diazeniumdiolated phosphorylcholine functional group is a copolymer. Alternatively, the biocompatible polymer is produced from a precursor polymer capable of containing a phosphorylcholine functional group selected from the group consisting of: methacrylate, polyester, polycarbonate, poly(ortho ester), polyamide, polyurethane, polyurea, poly(ester amide), polysulfone, polyketone, silicone, polyphosphazene, poly(amino acid), polyether, polyimide, vinyl polymer, polyacrylate, polymethacrylate, plystyrene, poly(vinyl acetate), poly(vinyl chloride), poly(vinyl ester), poly(vinyl ether), polyacrylonitrile, poly(vinyl ketone), poly(vinyl pyrolidinone), fluorinated polymer, natural or modified biopolymers, collagen, alginate, elastin, chitosan, fibrin, fibrinogen, cellulose, starch, collagen, dextran, dextrin, hyaluronic acid acid, heparin, glycosamino glycan, and polysaccharide; and combinations thereof.

In another embodiment, the precursor polymer is a methacrylate polymer according to Formula I:

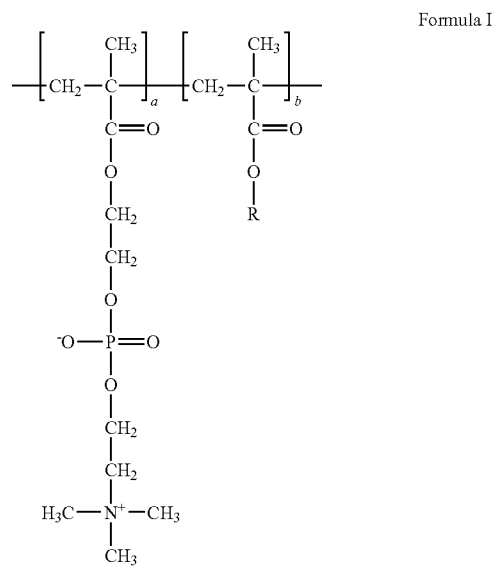

Formula I wherein R is $C_1$ to $C_{20}$ straight chain alkyl, $C_3$ to $C_8$ cycloalkyl, $C_2$ to $C_{20}$ alkenyl, $C_2$ to $C_{20}$ alkynyl, $C_2$ to $C_{14}$ heteroatom substituted alkyl, $C_2$ to $C_{14}$ heteroatom substituted cycloalkyl, $C_4$ to $C_{10}$ substituted aryl, or $C_4$ to $C_{10}$ heteroatom substituted heteroaryl; and further wherein a is 1 to 10,000 and b is 0 to 10,000.

The present disclosure also relates to a nitric oxide donating polymer comprising a biocompatible polymer of Formula II having at least one diazeniumdiolated phosphorylcholine functional group:

Formula II

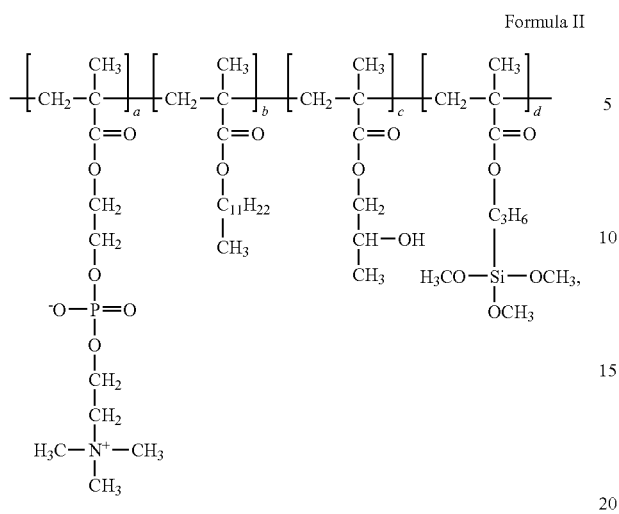

wherein a is 1 to 10,000 and b, c and d are each 0 to 10,000.

The present disclosure also relates to a medical device comprising a biocompatible polymer having at least one diazeniumdiolated phosphorylcholine functional group. In another embodiment of the medical device, the biocompatible polymer is a copolymer. In another embodiment of the medical device, the biocompatible polymer is produced from a precursor polymer capable of containing a phosphorylcholine functional group, said precursor polymer being selected from the group consisting of: methacrylate, polyester, polycarbonate, poly(ortho ester), polyamide, polyurethane, polyurea, poly(ester amide), polysulfone, polyketone, silicone, polyphosphazene, poly(amino acid), polyether, polyimide, vinyl polymer, polyacrylate, polymethacrylate, plystyrene, poly(vinyl acetate), poly(vinyl chloride), poly(vinyl ester), poly(vinyl ether), polyacrylonitrile, poly(vinyl ketone), poly(vinyl pyrolidinone), fluorinated polymer, natural or modified biopolymers, collagen, alginate, elastin, chitosan, fibrin, fibrinogen, cellulose, starch, collagen, dextran, dextrin, hyaluronic acid acid, heparin, glycosamino glycan, and polysaccharide; and combinations thereof.

In another embodiment of the medical device, the medical device is selected from the group consisting of a vascular stent, stent graft, urethral stent, biliary stent, catheter, suture, ocular device, heart valve, shunt, pacemaker, bone screw, bone anchor, protect plate and prosthetic device. In another embodiment of the medical device, medical device is a vascular stent.

In another embodiment of the medical device, the medical device further comprises at least one bioactive agent. In another embodiment of the medical device, the at least one bioactive agent is selected from the group consisting of zotarolimus, rapamycin or its derivatives, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, a therapeutic substance, an organic drug, a pharmaceutical compound, a recombinant DNA product, a recombinant RNA product, a collagen, a collagenic derivative, a protein, a protein analog, a saccharide, a saccharide derivative, and combinations thereof. In another embodiment of the medical device, the at least one bioactive agent is rapamycin and its derivatives.

The present disclosure also relates to a medical device comprising a nitric oxide donating polymer whose precursor polymer is a methacrylate polymer according to Formula I:

Formula I

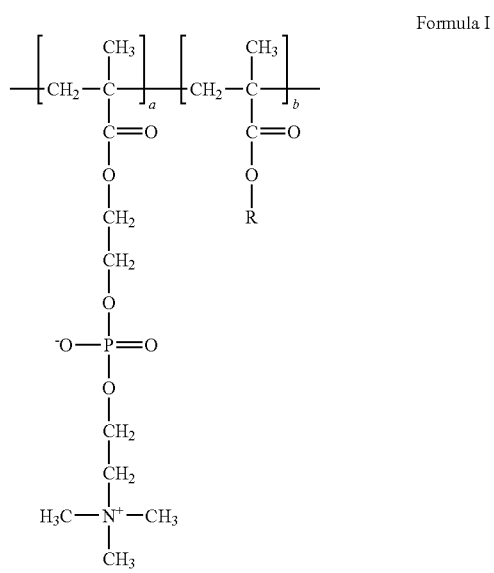

wherein R is $C_1$ to $C_{20}$ straight chain alkyl, $C_3$ to $C_8$ cycloalkyl, $C_2$ to $C_{20}$ alkenyl, $C_2$ to $C_{20}$ alkynyl, $C_2$ to $C_{14}$ heteroatom substituted alkyl, $C_2$ to $C_{14}$ heteroatom substituted cycloalkyl, $C_4$ to $C_{10}$ substituted aryl, or $C_4$ to $C_{10}$ heteroatom substituted heteroaryl; and further wherein a is 1 to 10,000 and b is 0 to 10,000.

In another embodiment, the medical device comprises a nitric oxide donating polymer comprising a biocompatible polymer of Formula II having at least one diazeniumdiolated phosphorylcholine functional group:

Formula II

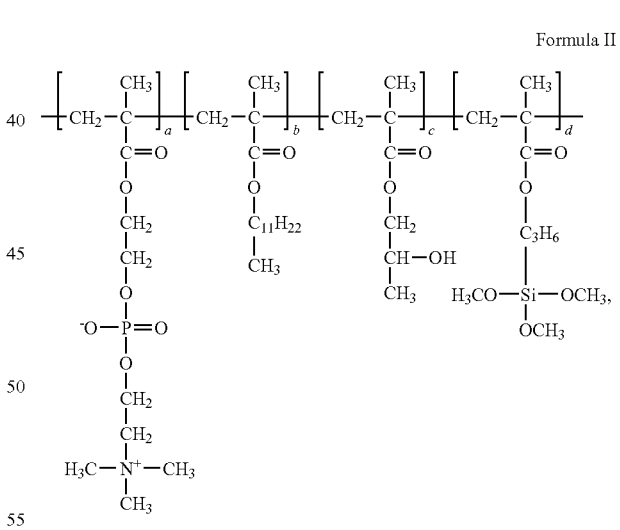

wherein a is 1 to 10,000 and b, c and d are each 0 to 10,000.

The present disclosure also relates to a method of making a nitric oxide donating polymer comprising: providing a biocompatible polymer having at least one phosphorylcholine functional group, diazeniumdiolating at least one of said phosphorylcholine functional groups to produce a biocompatible polymer having at least one phosphorylcholine diazeniumdiolated functional group. In another embodiment of the method of making a nitric oxide donating polymer, biocompatible polymer is produced from a precursor polymer capable of containing a phosphorylcholine functional group selected from the group consisting of: methacrylate, polyester, polycarbonate, poly(ortho ester), polyamide, polyurethane, polyurea, poly(ester amide), polysulfone, polyketone, silicone, polyphosphazene, poly(amino acid), polyether, polyimide, vinyl polymer, polyacrylate, polymethacrylate, plystyrene, poly(vinyl acetate), poly(vinyl chloride), poly(vinyl ester), poly(vinyl ether), polyacrylonitrile, poly(vinyl ketone), poly(vinyl pyrolidinone), fluorinated polymer, natural or modified biopolymers, collagen, alginate, elastin, chitosan, fibrin, fibrinogen, cellulose, starch, collagen, dextran, dextrin, hyaluronic acid acid, heparin, glycosamino glycan, and polysaccharide; and combinations thereof. In another embodiment of the present method, the biocompatible polymer is a copolymer.

In another embodiment of the method of making a nitric oxide donating polymer, the biocompatible polymer is represented by Formula II with at least one diazeniumdiolated phosphorylcholine functional group:

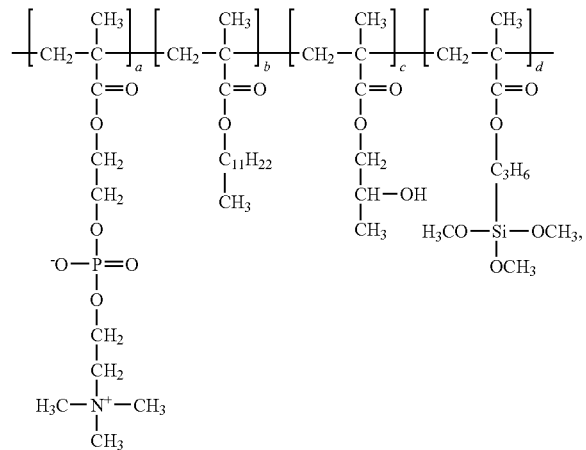

Formula II wherein a is 1 to 10,000 and b, c and d are each 0 to 10,000.

DETAILED DESCRIPTION OF THE INVENTION

The present disclosure provides polymers, methods of making polymers and medical devices having polymers which are capable of releasing nitric oxide and also have superior biocompatibility. Biocompatibility is made possible by the presence of at least one phosphorylcholine functional group on polymers which are used as precursors to the polymers. The at least one phosphorylcholine functional group on the precursor polymers is diazeniumdiolated to produce the polymers of the present disclosure which may be used to fabricate, coat, or otherwise be part of or included in one or more medical devices. Thus, the polymers of the present disclosure contain at least one diazeniumdiolated phosphorylcholine functional group capable of releasing therapeutic nitric oxide (NO). After release of nitric oxide the diazeniumdiolated phosphorylcholine functional group can potentially revert to back to a phosphorylcholine functional group on the polymer. Thus, after release of NO the polymer still retains its advantageous characteristic of superior biocompatibility.

In one embodiment, the present disclosure relates to a nitric oxide donating polymer comprising a biocompatible polymer having at least one diazeniumdiolated phosphorylcholine functional group.

As used herein "biocompatible" shall mean any material that does not cause injury or death to the animal or induce an adverse reaction in an animal when placed in intimate contact with the animal's tissues. Adverse reactions include inflammation, infection, fibrotic tissue formation, cell death, or thrombosis.

Phosphorylcholine is a molecule and a cell membrane component. Polymers having phosphorylcholine functional groups have been shown to be very biocompatible. The structure is phosphorylcholine is shown below:

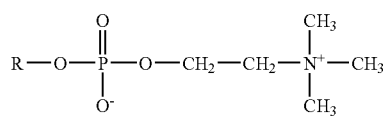

R can be any organic moiety.

As discussed herein a phosphorylcholine functional group is represented by:

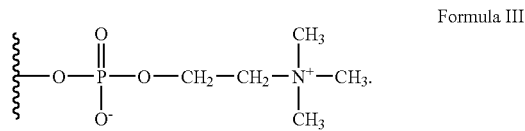 [SMILES: *OP(=O)([O-])OCC[N+](C)(C)C]

Formula III

As discussed herein a maximum diazeniumdiolated phosphorycholine functional group is represented by:

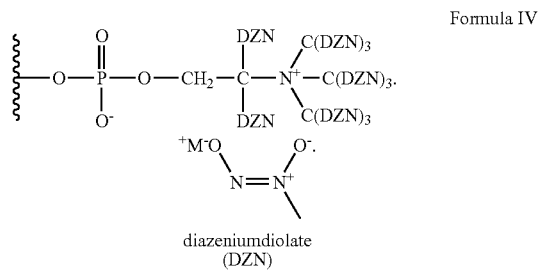

Formula IV

After H$_2$O/nitric oxide release/donation, the diazeniumdiolated phosphorylcholine functional group (Formula IV) can potentially go back to a phosphorylcholine functional group (Formula III).

It is within the scope and teachings of the present disclosure to cover any polymer which has at least one diazeniumdiolated phosphorylcholine functional group. Such polymers having at least one diazeniumdiolated phosphorylcholine functional group show superior biocompatibility and thus can be included in or serve as the framework for an apparatus such as an implantable medical device.

In one embodiment of the nitric oxide donating polymer, the polymer is a copolymer. As used herein "copolymer" refers to a macromolecule produced by the simultaneous or stepwise polymerization of two or more dissimilar monomeric units. Copolymer shall include, but not be limited to, bipolymers (two dissimilar units), terpolymer (three dissimilar units), etc.

The novel nitric oxide donating polymers of the present disclosure all include at least one diazeniumdiolated phosphorylcholine functional group as already stated. Such polymers will be produced from a precursor polymer capable of containing a phophosphorylcholine functional group which can then be diazeniumdiolated. Such precursor polymers, without limitation, maybe selected from the group consisting of: methacrylate, polyester, polycarbonate, poly(ortho ester), polyamide, polyurethane, polyurea, poly(ester amide), polysulfone, polyketone, silicone, polyphosphazene, poly(amino acid), polyether, polyimide, vinyl polymer, polyacrylate, polymethacrylate, plystyrene, poly(vinyl acetate), poly(vinyl chloride), poly(vinyl ester), poly(vinyl ether), polyacrylonitrile, poly(vinyl ketone), poly(vinyl pyrolidinone), fluorinated polymer, natural or modified biopolymers, collagen, alginate, elastin, chitosan, fibrin, fibrinogen, cellulose, starch, collagen, dextran, dextrin, hyaluronic acid acid, heparin, glycosamino glycan, and polysaccharide; and combinations thereof.

The present disclosure also relates to a nitric oxide donating polymer comprising a biocompatible polymer whose precursor polymer is a methacrylate polymer according to Formula I:

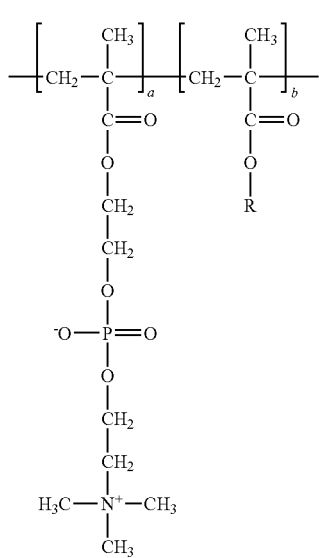

Formula I wherein R is C1 to C20 straight chain alkyl, C3 to C8 cycloalkyl, C2 to C20 alkenyl, C2 to C20 alkynyl, C2 to C14 heteroatom substituted alkyl, C2 to C14 heteroatom substituted cycloalkyl, C4 to C10 substituted aryl, or C4 to C10 heteroatom substituted heteroaryl; and further wherein a is 1 to 10,000 and b is 0 to 10,000.

The present disclosure also relates to a medical device comprising a biocompatible polymer having at least one diazeniumdiolated phosphorylcholine functional group.

In one embodiment, the present medical device can be a metallic medical device. When it is metallic, the medical device may include one or more of the following materials: stainless steel, nitinol, tantalum, a nonmagnetic nickel-cobalt-chromium-molybdenum [MP35N] alloy, platinum, titanium. Or it could be a combination thereof. The present polymers may be used to coat the metallic medical device. The coating steps as disclosed herein are made to medical device surfaces according to application in any manner known to those of ordinary skill in the art. A medical device surface to be coated in accordance with the present disclosure may be, for example, primed or bare. Coating application methods compatible with the present disclosure include, but are not limited to, spraying, dipping, brushing, and vacuum-deposition.

Physical properties of the polymers having at least one diazeniumdiolated phosphorylcholine polymers according to the present disclosure can be fine tuned so that these polymers can optimally perform for their intended use. Properties that can be fine tuned, without limitation, include Tg, molecular weight (both $M_n$ and $M_w$), polydispersity index (PDI, the quotient of $M_w/M_n$), degree of elasticity and degree of amphiphlicity. In one embodiment of the present invention, the Tg of the polymers range from about −10 .degrees Celsius. to about 85 degrees Cesius. In still another embodiment of the present invention, the PDI of the polymers range from about 1.35 to about 4. In another embodiment of the present invention, the Tg of the polymers ranges form about 0 degrees Celsius to about 40 degrees Celsius. In still another embodiment of the present invention, the PDI of the polymers range from about 1.5 to about 2.

As used herein "glass transition temperature," abbreviated ($T_g$) herein, refers to a temperature wherein a polymer structurally transitions from a elastic pliable state to a rigid and brittle state. As used herein $M_n$ refers to number-average molecular weight. Mathematically it is represented by the following formula:

$$M_n = \sum_i N_i M_i \bigg/ \sum_i N_i,$$

wherein the $N_i$ is the number of moles whose weight is $M_i$.

As used herein $M_w$ refers to weight average molecular weight that is the average weight that a given polymer may have. Mathematically it is represented by the following formula:

$$M_w = \sum_i N_i M_i^2 \bigg/ \sum_i N_i M_i,$$

wherein $N_i$ is the number of molecules whose weight is $M_i$.

As used herein "polydispersity index," abbreviated PDI herein, refers to the weight distribution of polymers in a sample. The polydispersity index is the fraction of the weight average molecular weight to the number-average molecular weight. Mathematically, it is represented by the following formula: $PDI=M_w/M_n$.

There are many theories that attempt to explain, or contribute to our understanding of how polymers adhere to surfaces. The most important forces include electrostatic and hydrogen bonding. However, other factors including wettability, absorption and resiliency also determine how well a polymer will adhere to different surfaces. Therefore, polymer base coats, or primers are often used and may be used in order to create a more uniform coating surface in accordance with the scope and teachings of the present disclosure.

The polymers according to the present disclosure may also be useful for the delivery and controlled or non-controlled release of drugs or bioactive agents. As used herein "controlled release" refers to the release of a bioactive compound from a medical device surface at a predetermined rate. Controlled release implies that the bioactive compound does not come off the medical device surface sporadically in an unpredictable fashion and does not "burst" off of the device upon contact with a biological environment (also referred to herein a first order kinetics) unless specifically intended to do so. However, the term "controlled release" as used herein does not preclude a "burst phenomenon" associated with deployment. In some embodiments of the present invention an initial burst of drug may be desirable followed by a more gradual release thereafter. The release rate may be steady state (commonly referred to as "timed release" or zero order kinetics), that is the drug is released in even amounts over a predetermined time (with or without an initial burst phase) or may be a gradient release. A gradient release implies that the concentration of drug released from the device surface changes over time. Bioactive agents suitable for release include, but are not limited to, zotarolimus, rapamycin or its derivatives, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, a therapeutic substance, an organic drug, a pharmaceutical compound, a recombinant DNA product, a recombinant RNA product, a collagen, a collagenic derivative, a protein, a protein analog, a saccharide, a saccharide derivative, and combinations thereof.

There are four specific attributes that stent coating polymers made in accordance with the teachings of the present invention should preferably but do not have to possess. The polymer compositions of the present invention should preferably be biocompatible, degrade at a predetermined rate, be elastic/ductile and possess a predetermined drug release profile. Other requirements include processing compatibility such as inert to sterilization methods including, but not limited to, ethylene oxide sterilization.

When the medical device of the present invention is used in the vasculature, the coating dimensions are generally measured in micrometers (μm). Coatings consistent with the teaching of the present invention may be a thin as 1 μm or a thick as 1000 μm. There are at least two distinct coating configurations within the scope of the present invention. In one embodiment of the present invention the drug-containing coating is applied directly to the device surface or onto a polymer primer. Depending on the solubility rate and profile desired, the drug is either entirely soluble within the polymer matrix, or evenly dispersed throughout. The drug concentration present in the polymer matrix ranges from 0.1% by weight to 80% by weight. In either event, it is most desirable to have as homogenous of a coating composition as possible. This particular configuration is commonly referred to as a drug-polymer matrix.

Finally, returning to coating thickness, while thickness is generally a minor factor in determining overall drug-release rates and profile, it is nevertheless an additional factor that can be used to tune the coatings. Basically, if all other physical and chemical factors remain unchanged, the rate at which a given drug diffuses through a given coating is directly proportional to the coating thickness. That is, increasing the coating thickness increases the elution rate and visa versa.

We now turn to another factor that contributes to the compatibilized, biodegradable controlled-release coatings of the present invention. As mentioned earlier, coating intended for medical devices deployed in a hemodynamic environment must possess excellent adhesive properties. That is, the coating must be stably linked to the medical device surface. All of these materials, and others, may be used with the controlled-release coatings made in accordance with the teachings of the present invention. Furthermore, the biodegradable polymers of the present invention can be used to fabricate an entire medical device such that the bioactive agent is dispersed throughout the polymer and released as the device degrades. This feature of the present invention is particularly useful when the device is implanted into remote regions of the body where subsequent removal, should it be required, is either not possible or involves complex, high risk surgical procedures Vascular stents present a particularly unique challenge for the medical device coating scientist. Vascular stents (hereinafter referred to as "stents") must be flexible, expandable, biocompatible and physically stable. Stents are used to relieve the symptoms associated with coronary artery disease caused by occlusion in one or more coronary artery. Occluded coronary arteries result in diminished blood flow to heart muscles causing ischemia induced angina and in severe cases myocardial infarcts and death. Stents are generally deployed using catheters having the stent attached to an inflatable balloon at the catheter's distal end. The catheter is inserted into an artery and guided to the deployment site. In many cases the catheter is inserted into the femoral artery or of the leg or carotid artery and the stent is deployed deep within the coronary vasculature at an occlusion site.

Vulnerable plaque stabilization is another application for coated drug-eluting vascular stents. Vulnerable plaque is composed of a thin fibrous cap covering a liquid-like core composed of an atheromatous gruel. The exact composition of mature atherosclerotic plaques varies considerably and the factors that affect an atherosclerotic plaque's make-up are poorly understood. However, the fibrous cap associated with many atherosclerotic plaques is formed from a connective tissue matrix of smooth muscle cells, types I and III collagen and a single layer of endothelial cells. The atheromatous gruel is composed of blood-borne lipoproteins trapped in the sub-endothelial extracellular space and the breakdown of tissue macrophages filled with low density lipids (LDL) scavenged from the circulating blood. (G. Pasterkamp and E. Falk. 2000. Atherosclerotic Plaque Rupture: An Overview. J. Clin. Basic Cardiol. 3:81-86). The ratio of fibrous cap material to atheromatous gruel determines plaque stability and type. When atherosclerotic plaque is prone to rupture due to instability it is referred to as "vulnerable" plaque. Upon rupture the atheromatous gruel is released into the blood stream and induces a massive thrombogenic response leading to sudden coronary death. Recently, it has been postulated that vulnerable plaque can be stabilized by stenting the plaque. Moreover, vascular stents having a drug-releasing coating composed of matrix metalloproteinase inhibitor dispersed in, or coated with (or both) a polymer may further stabilize the plaque and eventually lead to complete healing.

Treatment of aneurysms is another application for drug-eluting stents. An aneurysm is a bulging or ballooning of a blood vessel usually caused by atherosclerosis. Aneurysms occur most often in the abdominal portion of the aorta. At least 15,000 Americans die each year from ruptured abdominal aneurysms. Back and abdominal pain, both symptoms of an abdominal aortic aneurysm, often do not appear until the aneurysm is about to rupture, a condition that is usually fatal. Stent grafting has recently emerged as an alternative to the standard invasive surgery. A vascular graft containing a stent (stent graft) is placed within the artery at the site of the aneurysm and acts as a barrier between the blood and the weakened wall of the artery, thereby decreasing the pressure on artery. The less invasive approach of stent-grafting aneurysms decreases the morbidity seen with conventional aneurysm repair. Additionally, patients whose multiple medical comorbidities place them at an excessively high risk for conventional aneurysm repair are candidates for stent-grafting. Stent-grafting has also emerged as a new treatment for a related condition, acute blunt aortic injury, where trauma causes damage to the artery.

Once positioned at the treatment site the stent or graft is deployed. Generally, stents are deployed using balloon catheters. The balloon expands the stent gently compressing it against the arterial lumen clearing the vascular occlusion or stabilizing the aneurysm. The catheter is then removed and the stent remains in place permanently. Most patients return to a normal life following a suitable recovery period and have no reoccurrence of coronary artery disease associated with the stented occlusion. However, in some cases the arterial wall's intima is damaged either by the disease process itself or as the result of stent deployment. This injury initiates a complex biological response culminating is vascular smooth muscle cell hyperproliferation and occlusion, or restenosis at the stent site.

Recently significant efforts have been devoted to preventing restenosis. Several techniques including brachytherapy, excimer laser, and pharmacological techniques have been developed. The least invasive and most promising treatment modality is the pharmacological approach. A preferred pharmacological approach involves the site-specific delivery of cytostatic or cytotoxic drugs directly to the stent deployment area. Site-specific delivery is preferred over systemic delivery for several reasons. First, many cytostatic and cytotoxic drugs are highly toxic and cannot be administered systemically at concentrations needed to prevent restenosis. Moreover, the systemic administration of drugs can have unintended side effects at body locations remote from the treatment site. Additionally, many drugs are either not sufficiently soluble, or too quickly cleared from the blood stream to effectively prevent restenosis. Therefore, administration of anti-restenotic compounds directly to the treatment area is preferred.

Several techniques and corresponding devices have been developed to deploy anti-restenotic compounds including weeping balloon catheters and injection catheters. Weeping balloon catheters are used to slowly apply an anti-restenotic composition under pressure through fine pores in an inflatable segment at or near the catheter's distal end. The inflatable segment can be the same used to deploy the stent or a separate segment. Injection catheters administer the anti-restenotic composition by either emitting a pressurized fluid jet, or by directly piercing the artery wall with one or more needle-like appendage(s). Recently, needle catheters have been developed to inject drugs into an artery's adventitia. However, administration of anti-restenotic compositions using weeping catheters and injection catheters to prevent restenosis remains experimental and largely unsuccessful. Direct anti-restenotic composition administration has several disadvantages. When anti-restenotic compositions are administered directly to the arterial lumen using a weeping catheter, the blood flow quickly flushes the anti-restenotic composition downstream and away from the treatment site. Anti-restenotic compositions injected into the lumen wall or adventitia may rapidly diffuse into the surrounding tissue. Consequently, the anti-restenotic composition may not be present at the treatment site in sufficient concentrations to prevent restenosis. As a result of these and other disadvantages associated with catheter-based local drug delivery, investigators continue to seek improved methods for the localized delivery of anti-restenotic compositions.

The most successful method for localized anti-restenotic composition delivery developed to date is the drug-eluting stent. Many drug-eluting stent embodiments have been developed and tested. However, significant advances are still necessary in order to provide safe and highly effective drug delivery stents. One of the major challenges associated with stent-based anti-restenotic composition delivery is controlling the drug delivery rate. Generally speaking, drug delivery rates have two primary kinetic profiles. Drugs that reach the blood stream or tissue immediately after administration follow first-order kinetics. First-order drug release kinetics provide an immediate surge in blood or local tissue drug levels (peak levels) followed by a gradual decline (trough levels). In most cases, therapeutic levels are only maintained for a few hours. Drugs released slowly over a sustained time where blood or tissue concentrations remains steady follow zero-order kinetics. Depending on the method of drug delivery and tissue/blood clearance rates, zero-order kinetics result in sustained therapeutic levels for prolonged periods. Drug-release profiles can be modified to meet specific applications. Generally, most controlled release compositions are designed to provide near zero-order kinetics. However, there may be applications where an initial burst, or loading dose, of drug is desired followed by a more gradual sustained drug release (near zero-order kinetics). Nitric Oxide release from a medical device made in accordance with the teachings of the present invention is generally first order.

The term "medical device" as used herein refers to any device, product, equipment or material having surfaces that contact tissue, blood, or other bodily fluids in the course of their use or operation, which fluids are found in or are subsequently used in patients or animals. Medical devices include, for example, extracorporeal devices for use in surgery, such as blood oxygenators, blood pumps, blood storage bags, blood collection tubes, blood filters including filtration media, tubing used to carry blood and the like which contact blood which is then returned to the patient or animal. Medical devices also include endoprostheses implanted in a human or animal body, such as stents (such as vascular stents), pacemaker, pacemaker leads, heart valves, pulse generator, cardiac defibrillator, cardioverter defibrillator, spinal stimulator, brain and nerve stimulator, introducer, chemical sensor, and the like, that are implanted in blood vessels or the heart. Medical devices also include devices for temporary intravascular use such as catheters, guide wires, amniocentesis and biopsy needles, cannulae, drainage tubes, shunts, sensors, transducers, probes and the like which are placed into the blood vessels, the heart, organs or tissues for purposes of monitoring, repair or treatment. Medical devices also include prostheses such as hips or knees as well as artificial hearts. Medical devices also include implants, specula, irrigators, nozzles, calipers, forceps, retractors, stent grafts, urethral stents, biliary stents, catheters, sutures, ocular devices, heart valves, shunts, pacemakers, bone screws, bone anchors, protective place, prosthetic devices, vascular grafts, personal hygiene items, absorbable and nonabsorbable sutures, wound dressings, and the like. A selected medical device may be capable of being dry diazeniumdiolated according to the scope and teachings of the present disclosure.

The present disclosure also relates to a method of making a nitric oxide donating polymer comprising: providing a biocompatible polymer having at least one phosphorylcholine functional group, diazeniumdiolating at least one of said phosphorylcholine functional groups to produce a biocompatible polymer having at least one phosphorylcholine diazeniumdiolated functional group.

As stated above a phosphorylcholine functional group is represented by:

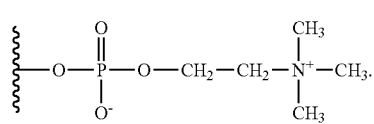

Formula III

Thus, to make a nitric oxide donating polymer in accordance with the scope and teachings of the present disclosure, a biocompatible polymer having at least one functional group as represented by Formula I is diazeniumdiolated. As a result a biocompatible polymer having at least one phosphorycholine diazeniumdiolated functional groups is produced. This is done in one embodiment with the use of strong base/nitric oxide.

A diazeniumdiolated phosphorycholine functional group is represented by:

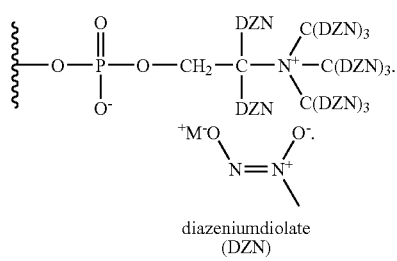

Formula IV diazeniumdiolate (DZN)

The term "diazeniumdiolating" or "diazeniumdiolation" as used herein, refers to the process of contacting a nucleophile residue with NO gas to produce a nitric oxide-releasing nucleophile residue complex containing the [N(O)NO] subunit. Reaction of the amine-functionalized polysilane with NO can occur by any method known in the art. Diazeniumdiolation can occur either through the neat exposure to NO gas or by immersing the coated substrate in an organic solvent and then exposing the solution to NO. Typical organic solvents include, for example, acetonitrile, diethyl ether, tetrahydrofuran, dioxane or mixtures thereof. In the solvent system, the NO gas can be bubbled into the solvent containing the coated substrate or added under mild or elevated pressure using typical equipment and methods known in the art. Additionally, any temperature can be used so long as it allows for the formation of at least one nitric oxide-releasing diazeniumdiolate group.

The present methods take advantage of the alpha protons to the positively charged nitrogen atom of phosphorylcholine moiety are acidic. Thus, under strong basic conditions, a carboanion nucleophile is produced which reacts with nitric oxide to form the diazeniumdiolated. One mole of phosphorylcholine may form eleven moles of diazeniumdiolated phosphorylcholine, thus capable of releasing up to 22 moles of nitric oxide. The present disclosure provides very efficient methods for NO loading.

EXAMPLES

Example 1

Preparation of Diazeniumdiolate

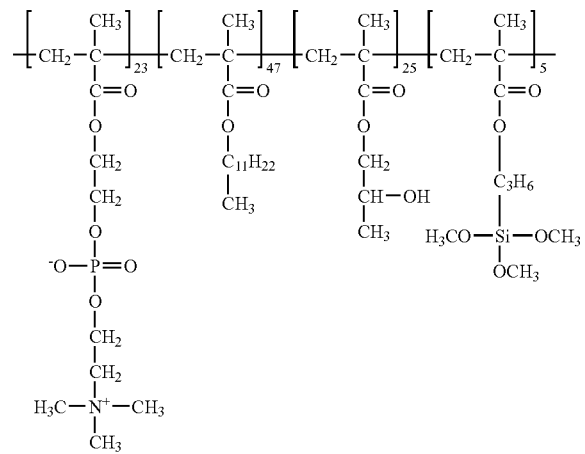

PC-1036 polymer 2.00 g of PC-1036 polymer was dissolved in 70 mL of THF and 10 mL of methanol. The solution was transferred to a 600 mL Parr reactor, and 16 mL of 1M sodium trimethylsilanolate in THF was added to give a clear solution. The reactor was sealed up and purged with argon through ten argon fill/vacuum cycles. Nitric oxide was charged into the apparatus at 80 psi. The reaction was stirred for 2 days. The pressure dropped to 60 psi. Polymer was isolated by evaporation of the solvent and solid polymer was washed with THF and dried at room temperature under vacuum.

Example 2

Nitric Oxide Release of Diazeniumdiolated PC Polymer 9.62 mg of the diazeniumdiolated polymer from example 1 wrapped in cloth was transferred to a test tube and added 5 mL of PBS buffer (pH=7.4). The test tube was incubated at 37° C. The nitric oxide released was accumulated for 8 minutes and swept out of the test tube with a 90 mL/min argon flow for 2 minutes and analyzed with NOA 280i (GE Analytical Instruments) nitric oxide analyzer. The accumulation and analysis cycle was controlled with an actuator. The diazeniumdiolated PC polymer released about 0.08 μmol/mg of nitric oxide in three days.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A nitric oxide donating polymer comprising:
a biocompatible polymer having at least one diazeniumdiolated phosphorylcholine functional group, wherein the polymer retains biocompatibility after release of nitric oxide from the diazeniumdiolated group under physiological conditions.

2. The nitric oxide donating polymer of claim 1, wherein said biocompatible polymer is a homopolymer, copolymer, random copolymer, block copolymer, graft polymer, hyperbranched polymer, dendrimer or thermoset polymer, or combinations thereof.

3. The nitric oxide donating polymer of claim 1, wherein said biocompatible polymer is produced from a precursor polymer capable of containing a phosphorylcholine functional group, said precursor polymer being selected from the group consisting of methacrylate, polyester, polycarbonate, poly(ortho ester), polyamide, polyurethane, polyurea, poly(ester amide), polysulfone, polyketone, silicone, polyphosphazene, poly(amino acid), polyether, polyimide, vinyl polymer, polyacrylate, polymethacrylate, plystyrene, poly(vinyl acetate), poly(vinyl chloride), poly(vinyl ester), poly(vinyl ether), polyacrylonitrile, poly(vinyl ketone), poly(vinyl pyrolidinone), fluorinated polymer, natural or modified biopolymers, collagen, alginate, elastin, chitosan, fibrin, fibrinogen, cellulose, starch, collagen, dextran, dextrin, hyaluronic acid, heparin, glycosamino glycan, and polysaccharide; and combinations thereof.

4. The nitric oxide donating polymer of claim 3, wherein said precursor polymer is a methacrylate polymer according to Formula I:

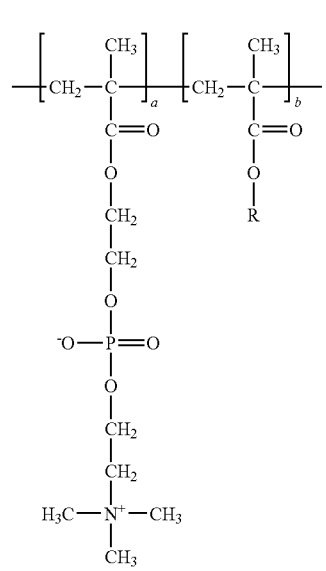

Formula I wherein R is $C_1$ to $C_{20}$ straight chain alkyl, $C_3$ to $C_8$ cycloalkyl, $C_2$ to $C_{20}$ alkenyl, $C_2$ to $C_{20}$ alkynyl, $C_2$ to $C_{14}$ heteroatom substituted alkyl, $C_2$ to $C_{14}$ heteroatom substituted cycloalkyl, $C_4$ to $C_{10}$ substituted aryl, or $C_4$ to $C_{10}$ heteroatom substituted heteroaryl; and further wherein a is 1 to 10,000 and b is 0 to 10,000; and wherein the polymer retains biocompatibility after release of nitric oxide from the diazeniumdiolated group.

5. A nitric oxide donating polymer comprising a biocompatible polymer having at least one diazeniumdiolated phosphorylcholine functional group, wherein said biocompatible polymer is produced from a precursor polymer of Formula II:

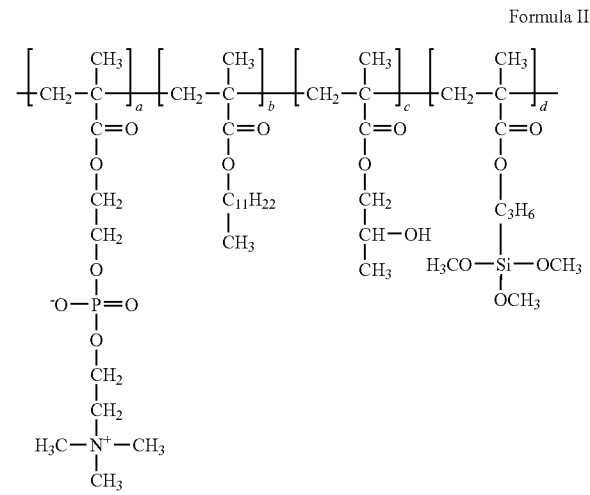

Formula II wherein a is 1 to 10,000 and b, c and d are each 0 to 10,000; and wherein the polymer retains biocompatibility after release of nitric oxide from the diazeniumdiolated group under physiological conditions.

6. A medical device comprising:
a biocompatible polymer having at least one diazeniumdiolated phosphorylcholine functional group, wherein the polymer retains biocompatibility after release of nitric oxide from the diazeniumdiolated group under physiological conditions.

7. The medical device of claim 6, wherein said biocompatible polymer is a copolymer.

8. The medical device of claim 6, wherein said biocompatible polymer is produced from a precursor polymer capable of containing a phosphorylcholine functional group, said precursor polymer being selected from the group consisting of: methacrylate, polyester, polycarbonate, poly(ortho ester), polyamide, polyurethane, polyurea, poly(ester amide), polysulfone, polyketone, silicone, polyphosphazene, poly(amino acid), polyether, polyimide, vinyl polymer, polyacrylate, polymethacrylate, plystyrene, poly(vinyl acetate), poly(vinyl chloride), poly(vinyl ester), poly(vinyl ether), polyacrylonitrile, poly(vinyl ketone), poly(vinyl pyrolidinone), fluorinated polymer, natural or modified biopolymers, collagen, alginate, elastin, chitosan, fibrin, fibrinogen, cellulose, starch, collagen, dextran, dextrin, hyaluronic acid, heparin, glycosamino glycan, and polysaccharide; and combinations thereof.

9. The medical device of claim 8, wherein said precursor polymer is a methacrylate polymer according to Formula I:

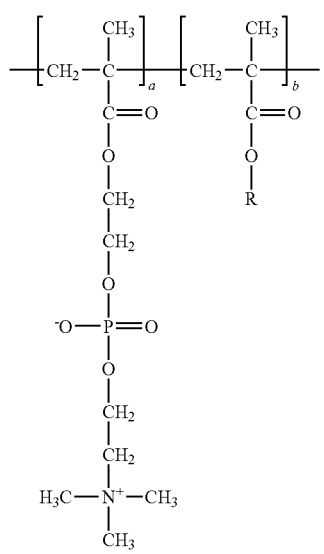

Formula I wherein R is $C_1$ to $C_{20}$ straight chain alkyl, $C_3$ to $C_8$ cycloalkyl, $C_2$ to $C_{20}$ alkenyl, $C_2$ to $C_{20}$ alkynyl, $C_2$ to $C_{14}$ heteroatom substituted alkyl, $C_2$ to $C_{14}$ heteroatom substituted cycloalkyl, $C_4$ to $C_{10}$ substituted aryl, or $C_4$ to $C_{10}$ heteroatom substituted heteroaryl; and further wherein a is 1 to 10,000 and b is 0 to 10,000.

10. The medical device of claim 6, wherein said medical device is selected from the group consisting of a vascular stent, stent graft, urethral stent, biliary stent, catheter, suture, ocular device, heart valve, shunt, pacemaker, bone screw, bone anchor, protect plate and prosthetic device.

11. The medical device of claim 6, wherein said medical device is a vascular stent.

12. The medical device of claim 6, wherein said medical device further comprises at least one bioactive agent.

13. The medical device of claim 12, wherein said at least one bioactive agent is selected from the group consisting of zotarolimus, rapamycin or its derivatives, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, a therapeutic substance, an organic drug, a pharmaceutical compound, a recombinant DNA product, a recombinant RNA product, a collagen, a collagenic derivative, a protein, a protein analog, a saccharide, a saccharide derivative, and combinations thereof.

14. The medical device of claim 12, wherein said at least one bioactive agent is rapamycin and its derivatives.

15. A medical device comprising a nitric oxide donating polymer comprising a biocompatible polymer having at least one diazeniumdiolated phosphorylcholine functional group, wherein said biocompatible polymer is produced from a precursor polymer of Formula II:

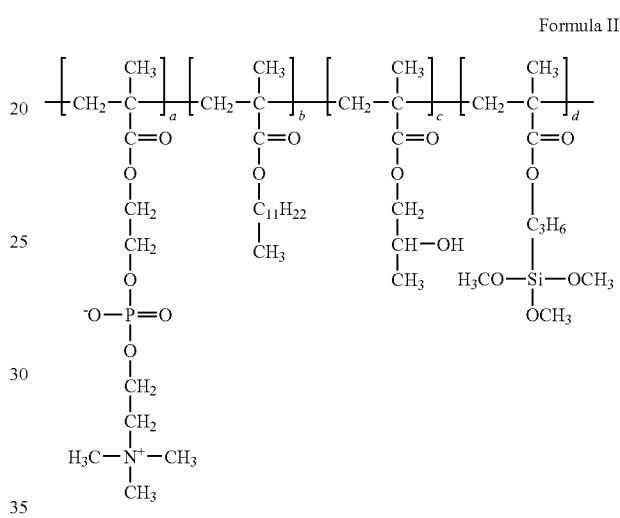

Formula II wherein a is 1 to 10,000 and b, c and d are each 0 to 10,000, wherein the polymer retains biocompatibility after release of nitric oxide from the diazeniumdiolated group under physiological conditions.

16. A nitric oxide donating polymer comprising a biocompatible polymer having at least one diazeniumdiolated phosphorylcholine functional group; wherein the polymer retains biocompatibility after release of nitric oxide from the diazeniumdiolated group under physiological conditions; wherein the diazeniumdiolated phosphorylcholine functional group comprises up to eleven diazeniumdiolate groups.

17. The nitric oxide donating polymer of claim 16 wherein the diazeniumdiolated phosphorylcholine functional group is represented by Formula

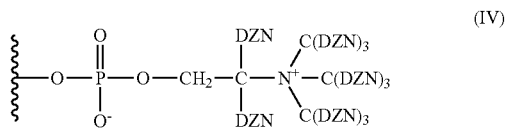

(IV)

wherein DZN is of the formula:

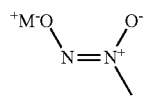

wherein M is a metal counterion or a proton.

18. A medical device comprising a biocompatible polymer having at least one diazeniumdiolated phosphorylcholine functional group, wherein the polymer retains biocompatibility after release of nitric oxide from the diazeniumdiolated group under physiological conditions; wherein the diazeniumdiolated phosphorylcholine functional group comprises up to eleven diazeniumdiolate groups.

19. The nitric oxide donating polymer of claim 18 wherein the diazeniumdiolated phosphorylcholine functional group is represented by Formula

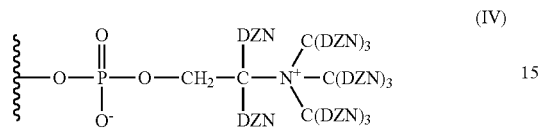

(IV)

wherein DZN is of the formula:

wherein M is a metal counterion or a proton.

* * * * *